(12) United States Patent
Mateu et al.

(10) Patent No.: US 7,682,605 B2
(45) Date of Patent: Mar. 23, 2010

(54) WATER-RESISTANT MASCARA COMPOSITION HAVING A HIGH WATER CONTENT

(75) Inventors: Juan R. Mateu, Oak Ridge, NJ (US); Domnica Cernasov, Ringwood, NJ (US); Ralph Macchio, Sparta, NJ (US)

(73) Assignee: Coty B.V., Haarlem (NL)

( * ) Notice: Subject to any disclaimer, the term of this patent is extended or adjusted under 35 U.S.C. 154(b) by 1413 days.

(21) Appl. No.: 10/527,281

(22) PCT Filed: Sep. 9, 2003

(86) PCT No.: PCT/EP03/10038

§ 371 (c)(1), (2), (4) Date: Mar. 9, 2005

(87) PCT Pub. No.: WO2004/032885

PCT Pub. Date: Apr. 22, 2004

(65) Prior Publication Data

US 2005/0265941 A1    Dec. 1, 2005

(30) Foreign Application Priority Data

Sep. 12, 2002    (DE)    .............. 102 44 117

(51) Int. Cl.
*A61Q 1/10*    (2006.01)
*A61Q 5/00*    (2006.01)
*A61K 8/92*    (2006.01)
*A61K 8/00*    (2006.01)

(52) U.S. Cl. .................. 424/70.7; 424/70.6; 424/70.12

(58) Field of Classification Search .............. 424/70.12, 424/70.6, 70.7
See application file for complete search history.

(56) References Cited

U.S. PATENT DOCUMENTS

| | | | |
|---|---|---|---|
| 4,457,784 A * | 7/1984 | Bernhard ................. 106/417 |
| 4,873,078 A * | 10/1989 | Edmundson et al. .......... 424/64 |
| 4,892,727 A * | 1/1990 | Grollier ..................... 424/69 |
| 5,013,763 A * | 5/1991 | Tubesing et al. ............ 514/772 |
| 5,126,136 A * | 6/1992 | Merat et al. ................. 424/401 |
| 5,207,998 A * | 5/1993 | Robinson et al. ............. 424/59 |
| 5,318,774 A * | 6/1994 | Alban et al. .................. 424/59 |
| 5,356,657 A | 10/1994 | Terada et al. |
| 5,451,405 A * | 9/1995 | Zhang et al. ................ 424/401 |
| 5,565,216 A * | 10/1996 | Cowsar et al. ............. 424/704 |
| 5,571,503 A * | 11/1996 | Mausner ..................... 424/59 |
| 5,800,825 A | 9/1998 | McMullen |
| 5,876,704 A | 3/1999 | Collin et al. |
| 6,033,648 A * | 3/2000 | Candau ........................ 424/59 |
| 6,074,652 A * | 6/2000 | Ishiwatari et al. .......... 424/401 |
| 6,214,329 B1 | 4/2001 | Brieva et al. |
| 6,296,860 B1 * | 10/2001 | Hasegawa et al. .......... 424/401 |
| 6,391,835 B1 * | 5/2002 | Gott et al. ................... 510/143 |
| 2002/0031488 A1 | 4/2002 | Bayer |
| 2002/0081322 A1 * | 6/2002 | Lawson et al. ............. 424/401 |
| 2002/0085984 A1 * | 7/2002 | DiGirolamo ................. 424/64 |

OTHER PUBLICATIONS

Isostearyl Palmitate. JEECHEM. http://www.jeen.com/cartexe/pdfs/spec%20JEECHEM%20ISP.pdf. Accessed Jan. 28, 2009.*
Q.S. Free Online Medical Dictionary. http://medical-dictionary.thefreedictionary.com/q.s. Accessed Jan. 30, 2009.*
Mascara. http://everything2.com/title/Mascara. Accessed on Aug. 23, 2009.*

* cited by examiner

*Primary Examiner*—Yvonne L Eyler
*Assistant Examiner*—Lori Mattison
(74) *Attorney, Agent, or Firm*—Novak Druce + Quigg; Gregory A. Nelson; Gregory M. Lefkowitz

(57) ABSTRACT

The invention relates to a water-resistant mascara composition that has a high water content. The inventive mascara composition contains an oil phase comprising a liquid ester, an oil, or a mixture thereof, 1 to 50 percent by weight of a silicon-based film-forming agent, 1 to 10 percent by weight of a gel-forming agent selected among fatty acid esters, glycol derivatives, or mixtures thereof, 1 to 50 percent by weight of substances selected among pigments, powders, fillers, and mixtures thereof, an aqueous phase comprising 42 to 75 percent by weight of water, 0.1 to 10 percent by weight of a surfactant, and other carrier substances, auxiliary agents, active substances, or mixtures thereof until reaching 100 percent by weight. Said composition contains no wax and no hydrocarbon solvent.

12 Claims, No Drawings

WATER-RESISTANT MASCARA COMPOSITION HAVING A HIGH WATER CONTENT

CROSS REFERENCE TO RELATED APPLICATION

This application is a national stage of PCT/EP2003/010038 filed Sep. 9, 2003 and based upon DE 102 44 117.0 filed Sep. 12, 2002 under the International Convention.

BACKGROUND OF THE INVENTION

1. Field of the Invention

The invention refers to a water-proof mascara composition which at the same time has a high water content.

2. Related Art of the Invention

Water-proof mascara compositions are already known. In many cases, such compositions contain cosmetic waxes. From U.S. Pat. No. 5,925,337 a waterproof mascara composition is known which contains 2-40% by weight of a wax, 5-15% by weight of a thickening agent, 35-50% by weight of a volatile organic solvent and 1-35% by weight of a water-soluble film-forming agent, wherein the last-named agent may e.g. also be an acrylate polymer. The composition does not contain any emulsifier. The water content of the aforesaid formulation is in the range of 7 to 12% by weight.

SUMMARY OF THE INVENTION

The object of the invention is to provide a mascara composition which has a very high water content, high gloss and at the same time is highly water-proof.

Another object is to develop a mascara which adheres well, but can easily be removed from the surface of the eyelashes with water.

Another object is to integrate substances such as talc, mica etc. into the mascara composition with no phase separation occurring.

BRIEF DESCRIPTION OF THE INVENTION

According to the invention, the aforesaid objects are achieved by means of a mascara composition which comprises a) an oil phase comprising a liquid ester, an oil or a mixture thereof, 1 to 50% by weight of a film-forming agent on a silicone base, 0.1 to 10% by weight of a gel-forming agent selected from among fatty acid esters, glycol derivatives and mixtures thereof;
b) 1 to 50% by weight of substances selected from among pigments, powders, fillers and mixtures thereof;
c) a water phase comprising 42 to 75% by weight of water;
d) 0.1 to 10% by weight of a surface-active agent; and
e) ad 100% by weight further carrier substances, auxiliaries, active agents or mixtures thereof, all percentages being relative to the total weight of the composition, and wherein the composition is free of waxes and hydrocarbon solvents.

DETAILED DESCRIPTION OF THE INVENTION

Since any wax added requires melting temperatures of up to 80° C. or above, it is advantageous to avoid the high melting temperatures both from an energetic point of view and with regard to the presence of temperature-sensitive ingredients, such as antioxidants, UV filters, etc., in the formulation.

The ester used for the oil phase can e.g. be Neopentyl Glycol Dioctanoate, Isopropyl Myristate, Diisopropyl Dimer Dilinoleate, Trimethylpropane Triisostearate, Triisostearyl Citrate, Cetearyl Octanoate, Distearyl Maleate, etc., in particular Diisostearyl Maleate.

Particularly suitable oils are e.g. silicone oils, mineral oils, Hydrogenated Polyisobutene, Polyisopren, Squalane, PPG-15 Stearyl Ether as well as vegetable oils. Silicone oils, such as e.g. Cyclomethicone, or mixtures of several siloxanes, such as Dimethicone, are preferred. Preferred ranges are 0.1 to 30% by weight.

A preferred silicone-based film-forming agent is Trimethyl Siloxysilicate or Amodimethicone or a mixture thereof.

The film-forming agent is preferably contained in the range of 20 to 30% by weight.

Normally, high contents of such film-forming agents reduce the viscosity of typical mascara compositions. In the composition according to the invention, the aforesaid decrease in viscosity does not occur, probably due to the presence of the special gel-forming agent.

If a fatty acid ester is used as gel-forming agent, it is preferably contained in the range of 0.1 to 5% by weight. A suitable fatty acid ester is e.g. Stearyl Behenate, preferably with a share of 0.8-4.0% by weight.

Examples of glycol derivatives are glycerol behenate, glycerol stearate, glycerol palmitate, glycerol arachidate. A preferred glycol derivate is Glycerol Behenate. The share of these glycol derivatives is preferably in the range of 1-4.5% by weight.

A special preferred gel-former is a mixture of glycol derivatives and fatty acid esters, such as a mixture of Glyceryl Behenate and Stearyl Behenate, preferably in a relation of 1:2 to 1:4.

The water phase, which can also contain auxiliaries and further active agents besides water, preferably comprises 50 to 75% by weight of water, more preferably 55 to 75% by weight and especially 57 to 68% by weight of water.

According to the invention, it is preferred that the surface-active agents be non-ionic surface-active agents, which can be added in the range of 0.5 to 7% by weight. They include coconut acyl mono or diethanol amides, alkyl polysaccharides, lactobionamides, ethyleneglycol esters, glycerol monoethers, polyhydroxyamides (glucamides), primary and secondary alcohol ethoxylates, especially the $C_{8-20}$ aliphatic alcohols ethoxylated with an average of from 1 to 20 moles of ethylene oxide per mole of alcohol. Mixtures of any of the foregoing surface active agents may also be used. A preferred is Dimethicone Copolyol (Cetyl PEG/PPG-10/1 Dimethicone).

Suitable pigments, pigment mixtures or powders with a pigment-like effect, also including those with a pearl-gloss effect, may include in the present invention, for example, iron oxides, aluminum silicates such as ochre, titanium (di)oxide, mica, kaolin, manganese containing clays such as umber and red bole, calcium carbonate, French chalk, mica-titanium oxide, mica-titanium oxide-iron oxide, bismuth oxychloride, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye.

They can be contained in the composition in the range of 0.1 to 50% by weight, preferably 7 to 15% by weight.

Pigments the surface of which has been treated can also be contained, e.g. such ones whose surface has been treated with alkyl silanes or perfluoroalcohol phosphates.

Additional cosmetic active agents which can be used in the present invention include e.g. inorganic and organic sunscreens, scavengers, moisturizing substances, vitamins, enzymes, vegetable active agents, polymers, melanin, antioxidants, antiinflammatory natural active agents, disintegration products of yeast or plant substances prepared by gentle ultrasonic treatment according to WO94/137983, kaolin as well as kaolin modified with SiO$_2$ according to WO94/17588.

The composition according to the invention can also advantageously contain antioxidants. Antioxidants include vitamins such as vitamin C and derivatives thereof, for example, ascorbic acetate, phosphate, and palmitate; vitamin A and derivatives thereof; folic acid and derivatives thereof; vitamin E and derivatives thereof, such as tocopheryl acetate; flavones or flavonoids; amino acids, such as histidine, glycine, tyrosine, tryptophan, and derivatives thereof; carotenoids and carotenes such as, for example, α-carotene, β-carotene; uric acid and derivatives thereof; α-hydroxy acids such as citric acid, lactic acid, malic acid; stilbene and derivatives thereof etc.

It is moreover advantageous to add to the compositions according to the invention corresponding water and/or oil soluble UVA or UVB filters or both. Advantageous oil-soluble UVB filters include 4-amino benzoic acid derivatives such as 4-(dimethylamino)-benzoic acid-(2-ethylhexyl) ester; esters of cinnamic acid such as 4-methoxy cinnamic acid (2-ethylhexyl) ester; benzophenone derivatives such as 2-hydroxy-4-methoxy benzophenone; 3-benzylidene camphor derivatives such as 3-benzylidene camphor.

Preferred oil-soluble UV filters are Benzophenone-3, Butyl Methoxybenzoylmethane, Octyl Methoxycinnamate, Octyl Salicylate, 4-Methylbenzylidene Camphor, Homosalate and Octyl Dimethyl PABA.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters include dibenzoyl methane derivatives such as 1-phenyl-4-(4'-isopropanol phenyl) propane-1,3-dione.

Further, thickeners for the water phase can be contained as auxiliaries, such as e.g. cellulose derivatives, hydrocolloids or salts of polyacrylates, such as e.g. Na-Polyacrylate.

Further auxiliaries can be solid esters, e.g. such ones having 18 or more carbon atoms in the alkyl part. For example these include Stearyl Behenate (octadecyl ester of docosanic acid) and others.

Preferred moisturizing substances are Glycerine, Butylene Glycol, Propylene Glycol or mixtures thereof which are contained in the range of 0.1 to 20% by weight.

The addition of electrolytes causes the solubility behaviour of an hydrophilic emulsifier to change. Hydrophilic emulsifiers are subject to a partial phase inversion during which the oil phase solubilizes water. The result is a stable emulsion, in particular a micro-emulsion or an O/W/O-emulsion. Suitable electrolytes are salts containing the following anions: chlorides, inorganic oxo-element anions, such as borates, aluminates, sulphates, phosphates, carbonates. Electrolytes based on organic anions include citrates, tartrates, lactates, propionates, acetates and benzoates as well as EDTA and salts thereof.

Cations of the salts can be alkali metal ions, alkaline earth metal ions, ammonium ions, alkyl ammonium ions, iron ions, zinc ions.

Electrolytes can be contained in the range of 0.01 to 5% by weight, preferably 0.1 to 2.5% by weight.

It has been found that the usual water contents of water proofed mascaras, which normally are below 20% by weight, can be considerably increased, namely up to a water content of 75% by weight. Further preferred ranges are 45-75%, especially 45-70 and special preferred 50-75% or 55-70% by weight.

In addition, the mascara according to the invention is water-proof, but can be washed off completely with warm water at a temperature of approximately 29° C. and above.

It is further surprising that such problematic substances as talc, mica and synthetic pearls, which have hydrophobic properties and tend to separate the water phase, can be made to form part of a stable cream-like emulsion due to the presence of thickeners, gums and emulsifiers, such as e.g. a cationic silicone polymer in the range of 0.1 to 20% by weight, preferably 0.1 to 10% by weight. Also formulations without any cationic silicone polymers are possible.

It has further been found that the mascara composition according to the invention has a high degree of brilliance (shine) despite the fact that higher amounts of silicones were used for the oil phase and the film-forming agent (e.g. Cyclomethicone/TMS) and normally such compositions containing silicone appear rather dull. The foregoing is another important advantage compared to known water-proof mascara compositions.

Since the mascara of the present invention is free of hydrocarbon solvents there is no special packaging required. A conventional water based mascaras package can be used for the water based waterproof mascara. This is very cost effective. No expenses are incurred in making new and higher density package that will accommodate hydrocarbon solvent-based mascaras or the tooling needed to make said package.

Further the mascara of the present invention shows after a clinical testing report waterproofness at least at the same level than products of the market and further it shows no streaking, smudging, flaking and/or fading as a statistical significant increase after 3 immersions at a baseline visit and a 6 hour visit (study with 28 female panellists with usual inclusion and exclusion criteria).

In the following, the invention shall be described in detail by examples. All percent figures are by weight if not other set out.

EXAMPLE 1

Mascara I

| Phase A | |
|---|---|
| Purester 40 | 3.5 |
| Distearyl Maleate | 0.5 |
| Glyceryl Behenate | 1.0 |
| (1:1) Cyclomethicone/Trimethyl Siloxysilcate (TMS) | 22 |
| Dimethicone Copolyol | 1.1 |
| Preservative | 0.8 |
| Propylene Glycol | 1.5 |
| Glycerine | 0.6 |
| Phase B | |
| Iron oxide, black | 7.8 |
| Phase C | |
| Water | 57 |
| Sodium chloride | 0.2 |
| Phase D | |
| Dimethicone | 4 |

Phase A is mixed at 200-1000 rpm and heated to about 75° C. until homogenous. Introducing Glycerine and PPG to Cyclomethicone/TMS will gel into a stable creamy paste. Phase B is incorporated at the same conditions as phase A. Phase C is mixed at 100-400 rpm, heated to about 70° C. and incorporated to the mixture of A and B maintaining the temperature and with 800-2000 rpm. The mixture is cooled down while mixing to 45-50° C. After that phase D is added and the batch was cooled to 25-30° C.

EXAMPLE 2-4

Mascara II, III and IV

|  | II | III | IV |
|---|---|---|---|
| DISM Diisostearyl Maleate | 0.5 | 1 | 0.5 |
| (1:1) Cyclomethicone/TMS | 22 | 21 | 20 |
| Dimethicone Copolyol | 1.4 | 2 | 2 |
| Preservative | 0.5 | 0.5 | 0.5 |
| Iron oxide, black | 6.8 | 6.8 | 6.8 |
| Water | | q.s. ad 100 | |
| Purester 40* | 3 | 3.3 | 3 |
| Glyceryl Behenate | 1 | 2 | 1.2 |
| Mica 8 As | 1 | 1 | 1 |
| Amodimethicone | 1 | 0.8 | 0.8 |
| Merguard 1105 | 0.3 | 0.1 | 0.1 |
| Sodium Chloride | 0.4 | 0.6 | 0.6 |
| Butylene Glycol | 1.5 | 2.5 | 2.5 |
| Glycerine | 0.6 | 1 | 1 |
| Cyclomethicone | — | — | 2 |

*Stearyl Behenate & Methyl Behenate & Stearyl Alcohol
The preparation of the mascara was like example 1.

EXAMPLE 5

Comparison Test Gloss

Gloss measurements were made using a Glossgard System 60 instrument (Gardner Instruments) at an 85 degree angle. This glossmeter is good for measuring semi-glossy surfaces such as mascara, lip and nail products. It has a statistical software built into the unit for mean calculation of repeated readings.

The measurements were made on a 6 mil (about 150 μm) thick drawdown which was allowed to air dry for 24 hrs. The substrate was a Leneta form 5c-opacity drawdown card.

Comparison measurements were made between two waterproof mascaras of the market (A, B) and one non-waterproof gloss mascara (C) and the waterproof mascara of the present invention (D). Results at 85 degree angle:

| A | 2.7 | C | 27.8 |
|---|---|---|---|
| B | 0.6 | D | 79.6 |

The measurements show the superiority of the product of the present invention also in the gloss attribute.

We claim:
1. A water-proof mascara composition which comprises
a) an oil phase comprising
   (i) 0.1 to 30% by weight of an oil,
   (ii) 1 to 50% by weight of a silicon-based film-forming agent, and
   (iii) 0.1 to 10% by weight of a gel-forming agent being a mixture of glyceryl behenate and stearyl behenate in a ratio of 1:2 to 1:4;
b) 7 to 15% by weight of pigments, powders-with pigment like effects, or mixtures thereof;
c) a water phase comprising 42 to 75% by weight of water;
d) 0.1 to 10% by weight of a surface active agent; and
e) further carrier substances, auxiliaries, active agents or mixtures thereof, all percentages being relative to the total weight of the composition, wherein the composition is free of waxes and hydrocarbon solvents, wherein said water-proof mascara composition comprises an emulsion, and wherein the applied water-proof mascara composition exhibits no statistically increased amount of streaking, smudging or flaking after immersion in water.

2. The composition according to claim 1, wherein the oil of the oil phase is a silicone oil.

3. A mascara composition according to claim 1 comprising an oil phase which comprises a liquid ester, 15 to 30% by weight of said silicon-based film-forming agent, and 0.1 to 10% by weight of said gel-forming agent being a mixture of glyceryl behenate and stearyl behenate in a ratio of 1:2 to 1:4;
7 to 15% by weight of said pigments selected from the group consisting of: iron oxides, mica, talc, kaolin, manganese containing clays, nylon pearls, coated pigments and mixtures thereof;
a water phase comprising 45 to 70% by weight of water; 0.5 to 7% by weight of a nonionic surface-active agent; 0.8 to 2% by weight of a cationic silicone polymer; and optionally, further carrier substances, auxiliaries, active agents or mixtures thereof, wherein the composition is free of waxes and hydrocarbon solvents.

4. The composition according to claim 3 wherein the ester of the oil phase is diisostearyl maleate.

5. The composition according to claim 1, wherein the gel-forming agent is in the range of 0.1-5% by weight.

6. The composition according to claim 1, wherein the composition comprises as a film-forming agent trimethyl siloxysilicate.

7. The composition according to claim 1, wherein the water phase comprises 50 to 75% by weight water.

8. The composition according to claim 7, wherein the water phase comprises 56 to 75% by weight water.

9. The composition according to claim 1, wherein the surfactant is a nonionic surfactant.

10. The composition according to claim 1 wherein the composition contains moisturizing substances selected from the group consisting of: propylene glycol, butylene glycol, glycerine, and mixtures thereof.

11. The composition according to claim 1, wherein the gel-forming agent is in the range of 1.0-4.5% by weight.

12. A water-proof mascara composition which comprises
a) an oil phase comprising
   (i) 0.1 to 30% by weight of, an oil,
   (ii) 1 to 50% by weight of a silicon-based film-forming agent, and
   (iii) 0.1 to 10% by weight of a gel-forming agent being a mixture of glyceryl behenate and stearyl behenate in a ratio of 1:2 to 1:4;
b) 1 to 50% by weight of substances selected from the group consisting of: pigments, powders, fillers and mixtures thereof;
c) a water phase comprising 42 to 75% by weight of water;
d) 0.1 to 10% by weight of a surface-active agent; and
e) further carrier substances, auxiliaries, active agents or mixtures thereof, all percentages being relative to the total weight of the composition, wherein the composition is free of waxes and hydrocarbon solvents, wherein said water-proof mascara composition comprises an emulsion.

* * * * *